United States Patent
Tomita et al.

[11] Patent Number: 5,130,600
[45] Date of Patent: Jul. 14, 1992

[54] ACCELERATION SENSOR

[75] Inventors: Tomonobu Tomita; Yoshinao Mukasa; Masahiro Sasaki; Fumio Ohta; Kazuo Yorihiro, all of Yokkaichi, Japan

[73] Assignee: Mitsubishi Petrochemical Co., Ltd., Tokyo, Japan

[21] Appl. No.: 530,162

[22] Filed: May 29, 1990

[30] Foreign Application Priority Data

Jun. 2, 1989 [JP] Japan .................... 1-140508
Jun. 2, 1989 [JP] Japan .................... 1-140509

[51] Int. Cl.$^5$ ............................ H01L 41/08
[52] U.S. Cl. ................... 310/329; 73/654; 310/344; 310/346; 310/319
[58] Field of Search ......... 310/329, 319, 340, 344, 310/346, 348, 800; 73/517 R, 654

[56] References Cited

U.S. PATENT DOCUMENTS

| | | | |
|---|---|---|---|
| 2,509,478 | 5/1950 | Caroselli | 310/346 |
| 3,441,754 | 4/1969 | Heny | 310/346 |
| 4,356,423 | 10/1982 | Gudzin | 310/338 |
| 4,825,117 | 4/1989 | Thomas, III et al. | 310/346 |
| 5,030,875 | 7/1991 | Knecht | 310/346 |

Primary Examiner—Mark O. Budd
Attorney, Agent, or Firm—David O'Reilly

[57] ABSTRACT

This invention relates to an acceleration sensor having less output drift due to temperature change and noise due to external induction which includes a piezoelectric device formed of a piezoelectric member having one or more electrodes provided on each of sides thereof and a lining member of low linear expansion coefficient adhered to one side thereof. A low linear expansion coefficient circuit substrate is provided having the piezoelectric device adhered to one side thereof and having a signal processing electronic circuit formed on the other side thereof. A cabinet having three layers, including an internal conductive resin layer, an adiabatic resin layer, and an external conductive metal layer, completely enclose the piezoelectric device and the circuit substrate.

18 Claims, 5 Drawing Sheets

ACCELERATION SENSOR

FIELD OF THE INVENTION

The present invention relates to an acceleration sensor for detecting an acceleration with a piezoelectric member. More particularly, it relates to an acceleration sensor to be mounted on a vehicle for use at a low frequency without influences by changes of environmental temperature and source voltage and electromagnetic noises.

BACKGROUND OF THE INVENTION

Acceleration is obtained by differentiation of displacement two times. The actual acceleration is low even for a large displacement with a lower frequency. As examples, for a displacement of 10 micrometers at 160 Hz, the acceleration is 1 G; for a displacement of 10 m at 0.16 Hz, it is 1 G. In a vibration measurement at a lower frequency, the actual displacement is as small as 1 m maximum. For a low frequency of 1.6 Hz, for example, the acceleration is 0.1 G with displacement of 1 cm.

Accordingly, in order to measure a vibration of 0.1 to 10 Hz, it is necessary to measure acceleration as low as 0.1 to 0.01 G.

The inventors have filed an application for an acceleration sensor for use at lower frequencies as Japan Utility Model No. 63-103602. The mentioned acceleration sensor is constructed with a piezoelectric device enclosed by a conductive resin, an adiabatic member, and a thermally conductive member in that order. The enclosed piezoelectric device is mounted on an insulative substrate, and a capacitor, for preventing possible external inductive noises, is connected between the conductive resin and the electrically-conductive thermally conductive member. In this construction, the electrically-conductive resin can electromagnetically shield the piezoelectric device. The piezoelectric device is free from adverse effects of possible external electrical noises. With use of the adiabatic member and thermal conductive, also, it is possible to considerably reduce adverse effects due to a possible temperature change by external heating or cooling. The piezoelectric device 6, further, is electrically isolated from a matter to be measured by means of the insulative substrate. Thus, it cannot be subjected to possible inductive noises, such as an electrostatic induction and a potential to ground. The capacitor for preventing possible external inductive noises that is connected between the conductive resin and the electrically-conductive thermally conductive member can by-pass possible external radio-frequency noises. This is effective in higher precision measurement for low-frequency, low accelerations.

However, the prior art mentioned above must have the capacitor to prevent possible external inductive noises connected between the conductive resin and the electrically-conductive thermal conductive in order to by-pass possible external radio-frequency noises. This frequently proves to be an inconvenience in an environment, since the construction is complicated as such. In addition, the prior art must have an additional cable for connecting an output of the piezoelectric device to a separate signal processing electronic circuit. This also frequently proves to be an inconvenience in that the construction cannot be small-sized or handy and that possible external inductive noises could occur between the piezoelectric device and related electronic circuits. Further, since the piezoelectric member is not supported by a member having a linear expansion coefficient of less than the one, the sensitivity of the sensor cannot be constant with a change of environmental temperature.

SUMMARY OF THE INVENTION

The disadvantages of the prior art discussed above are overcome by the present invention. Accordingly, it is an object of the present invention to provide a new acceleration sensor that is shown in the accompanying drawings. A piezoelectric member 1 has electrodes provided on both sides thereof. A lining member 5 of a low linear expansion coefficient is adhered to one side of the piezoelectric member 1 to form a piezoelectric device 6. This piezoelectric device 6 is adhered to one side of a circuit substrate 7 of a low linear expansion coefficient. This circuit substrate 7 has a signal processing electronic circuit 8 formed on the other side thereof. The above-mentioned matters and circuit are entirely enclosed by three layers, including an internal conductive resin layer 10, an adiabatic resin layer 9, and an external conductive matal layer 11.

The acceleration sensor according to the present invention can be made compact and small in size and cannot be subjected to possible external inductive noises between the piezoelectric device 6 and the signal processing electronic circuit 8, since no cable is provided to connect an output of the piezoelectric device 6 to the signal processing electronic circuit 8. Also, since the piezoelectric member 1 is supported by a member having a linear expansion coefficient of less than the one thereof, sensitivity of the sensor can be constant with a change of environmental temperature.

BRIEF DESCRIPTION OF THE DRAWINGS

These and other objects and features of the invention will be better understood upon consideration of the following detailed description and the accompanying drawings in which.

DETAILED DESCRIPTION OF THE PREFERRED EMBODIMENT

Figure 1:
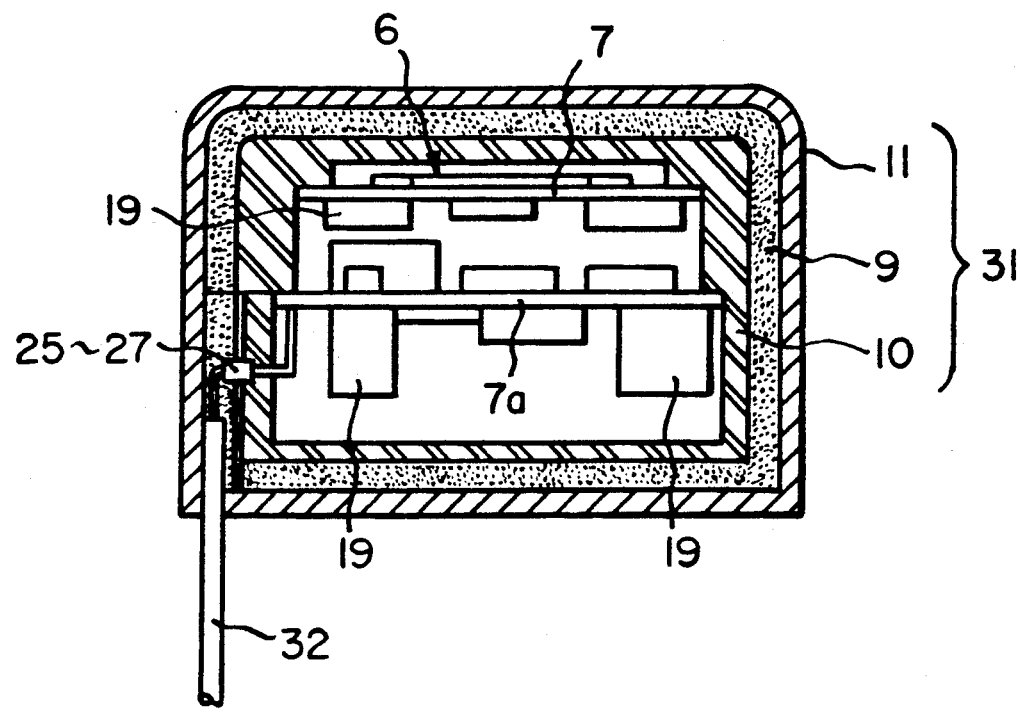
FIG. 1 is a brief cross-sectional view of an illustrative embodiment of the present invention for an acceleration sensor.
Figure 2:
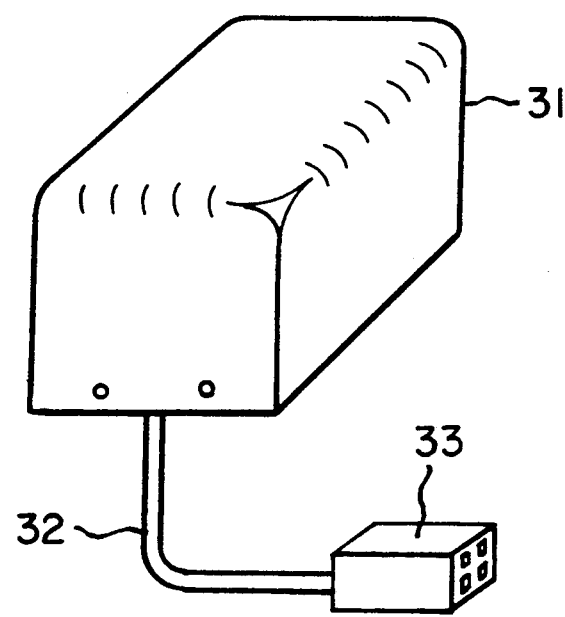
FIG. 2 shows the appearance of the illustrative embodiment.

The present invention is illustrated in further detail by reference to the accompanying drawings in which:

FIG. 1 is a brief cross-sectioned view of an embodiment of the novel acceleration sensor according to the present invention. FIG. 2 is a perspective view illustrating the appearance of the embodiment. FIG. 3 is an illustrative perspective view showing construction of the preferred embodiment.

Figure 3A:
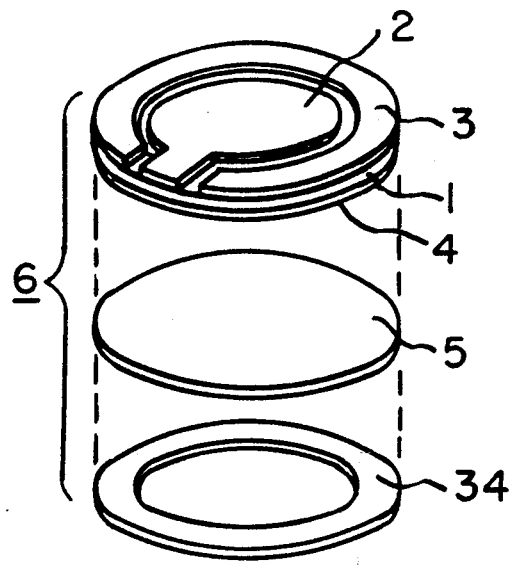
FIGS. 3(a) through 3(c) are illustrative perspective views of the illustrative embodiment.
Figure 3B:
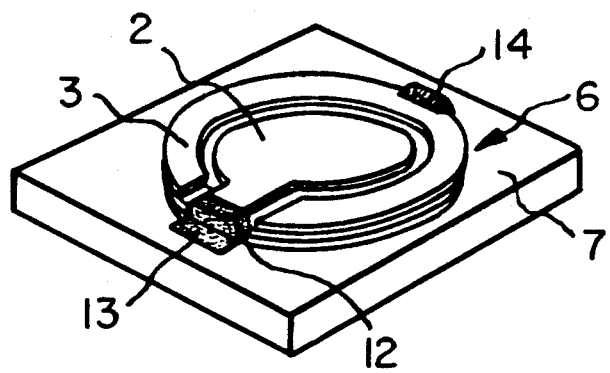
Figure 3C:
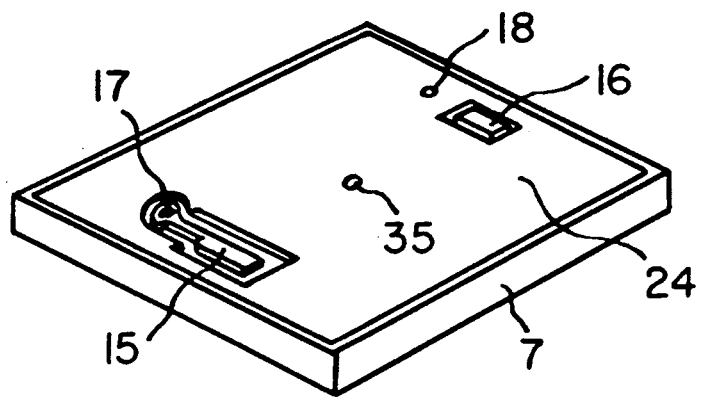
Figure 4:
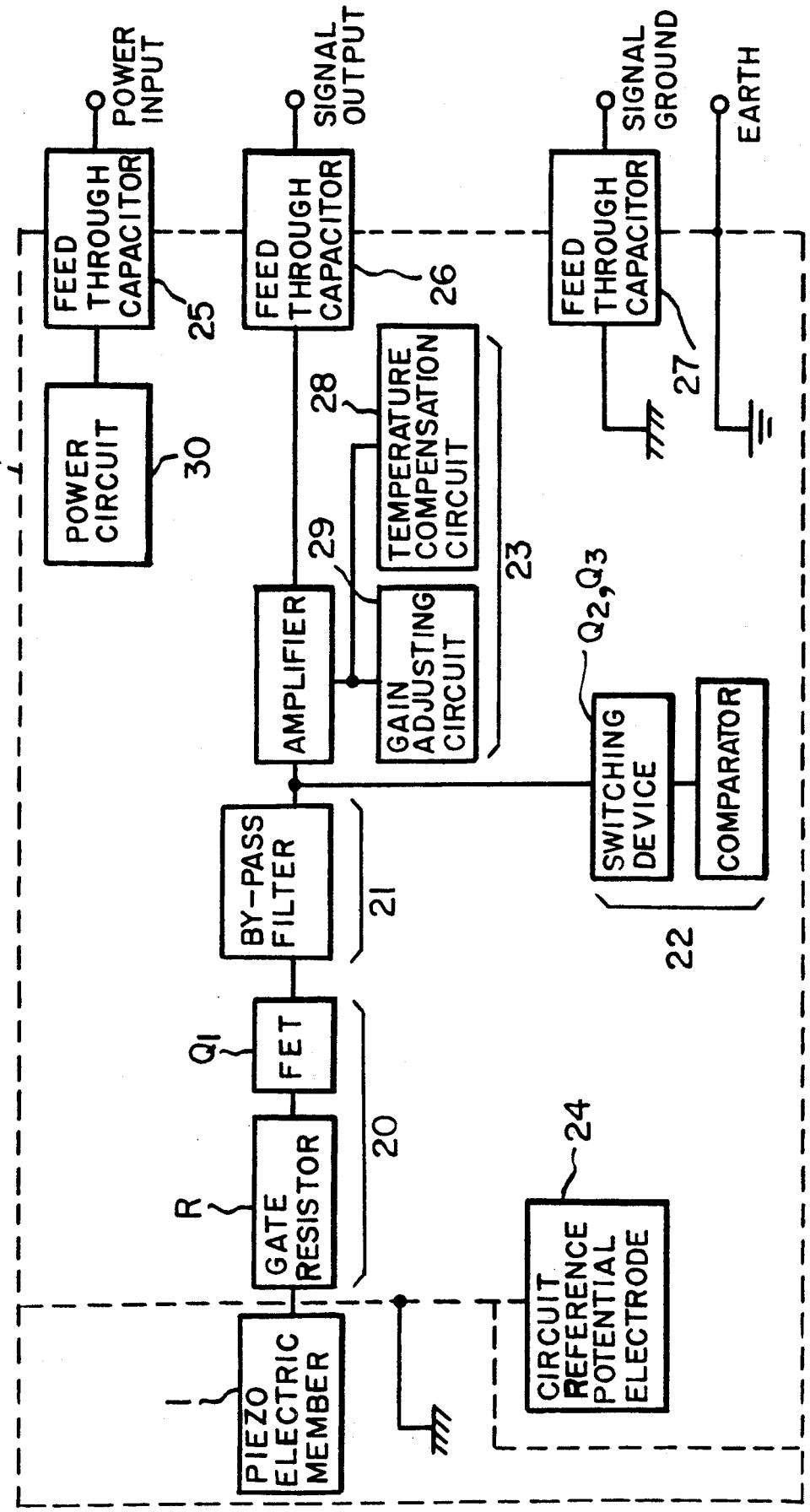
FIG. 4 is a block diagram showing an example of a signal processing electronic circuit of the illustrative embodiment.

A number 1 in FIGS. 3(a), 3(b), and 4 indicates a piezoelectric member. Piezoelectric member 1 is a sheet of piezoelectric resin 10 to 500 micrometers thick having a volume specific resistance of $10^{12}$ to $10^{14}$ ohm-cm at 20 degrees Celsius. It may be one of the high polymer piezoelectric materials, such as a polyvinylidene Fluoride (PVDF) resin and copolymerized polyvinylidene cyanide/vinyl acetate P(VDCN/VCA) resin. It also may be one of high polymer compounds, such as a composition of Lead-zirconate-titanate (PZT), polyacetal (POM) resin, copolymerized acrylonitrile-butadiene rubber (NBR), and carbon. The rubber can be vulcanized to improve its durability. Piezoelectric member 1 further may be piezoelectric material composed of calcium-substituted Lead-titanate (PCT) and urethane-denatured polyacetal (u-POM) resin.

Piezoelectric device 6 is formed in a way that piezoelectric member 1 has electrodes provided on both sides thereof by means of evaporation, sputtering, conductive paint printing, or the like, and one of the electrodes has a lining member 5 adhered on one side. It is preferable to mount supporting member 34 on a circumference of lining member 5. It is effective to reduce pyro-electricity in a way, for example, as shown in FIG. 3. Piezoelectric member 1 has a pair of electrodes, positive electrode 2 and negative electrode 3, attached on one side thereof, and neutral electrode 4 provided on the other side thereof on which the lining member 5 is provided on which the supporting member 34 is provided. The effect can be further increased if the areas of positive electrode 2 and negative electrode 3 are made equal.

Also, it is effective to reduce unnecessary electrical noises in a way that piezoelectric member 1 has positive electrode 2 arranged o n a central portion of one side thereof, and has negative electrode 3 arranged on a circumference of the same side.

Of course, an electrically insulating zone is provided between inside positive electrode 2 and outside negative electrode 3. For lining member 5 an epoxy resin can be used reinforced with glass fiber, polyimid, polyester, or similar materials having a linear expansion coefficient less than $5 \times 10^{-5}$ degree Celsius. The linear expansion coefficients of piezoelectric member 1, lining member 5, and circuit substrate 7 should be selected to be smaller in this order. The thickness of lining member 5 should be 0.01 to 1.6 mm, preferably 0.03 to 0.5 mm. This thickness should be ⅓ to 10 times that of piezoelectric member 1.

Lining member 5 is adhered to one side of piezoelectric member 1 with an adhesive agent. This makes lining member 5 greatly contribute with respect to vibration. Thus, piezoelectric device 6 provides a constant sensitivity gradient with respect to temperature.

Supporting member 34 can use an epoxy resin reinforced with glass fiber, ceramics, metals, or similar materials, the linear expansion coefficient of which, are approximate to or lower than that of lining member 5.

Supporting member 34 is suitably shaped like a dish, ring, or similar forms that should have a recess or hole on a central portion thereof.

The size of positive electrode 2, negative electrode 3, and supporting member 34 are determined by:

$$A/2 \leq C \leq B \leq D$$

where A is the outside diameter of inside positive electrode 2, B is the outside diameter of outside negative electrode 3, C is the inside diameter of supporting member 34, and D is the outside diameter of supporting member 34. The sizes are preferably determined by $$A \leq C \leq (B-A) \times \tfrac{1}{2} + A < B \leq D.$$

The supporting member 34 is adhered to lining member 5 with a adhesive agent to form piezoelectric device 6.

A continuous space is provided above and below piezoelectric device 6 in order to provide a linear output characteristic thereof to an exciting force.

Piezoelectric device 6 is adhered to one side of circuit substrate 7 having low linear expansion coefficient. Circuit substrate 7 has signal processing electronic circuit 8 formed on the other side thereof.

Circuit substrate 7 can be glass epoxy resin, ceramics (alumina, silicon wafer, etc.), metals, or similar materials having a linear expansion coefficient less than $5 \times 10^{-5}$/degree Celsius, a thickness of 0.2 to 5 mm, and a rigidity sufficient to endure a possible strain due to differences of linear expansion coefficients of circuit substrate 7 and cabinet 31.

A space enclosed by lining member 5, supporting member 34, and circuit substrate 7 communicates with outside space in order to prevent inside pressure from being changed with temperature. For this communication, it is preferable to provide feed-through hole 35 on circuit substrate 7. Feed-through hole 35 also may be provided on piezoelectric member 1 or lining member 5.

In order to connect positive electrode 2 on piezoelectric member 1 and negative electrode 3 to signal processing electronic circuit 8 on circuit substrate 7, a connection circuit is formed by connection lead wires by wire adhereing, thin film by evaporation, sputtering, or similar process, thick film circuit printing, conductive painting, or similar processes.

In order to avoid possible short-circuit of the connection circuit with neutral electrode 4 prior to wiring, it is coated by an insulating material 12. Then, positive electrode 2 and the negative electrode 3 of piezoelectric device 6 are connected to positive electrode pattern 15 and negative electrode pattern 16 formed on one side of circuit substrate 7 through positive electrode lead pattern 13 and a negative electrode lead pattern 14, respectively (FIG. 3). Positive electrode pattern 15 and negative electrode pattern 16 are connected to signal processing electronic circuit 8 formed on the other side of circuit substrate 7 through feed-through hole 17 and feed-through hole 18, respectively. Circuit reference potential electrode 24 is integrated with negative electrode pattern 16 as formed.

Signal processing electronic circuit 8, for example, as shown in FIG. 1, can be divided into circuit substrate 7 and circuit substrate 7a as formed. Component parts 19 form signal processing electronic circuit 8.

Signal processing electronic circuit 8, for example, as shown in FIG. 4, is constructed of impedance transducer 20, by-pass filter 21, muting section MC 22, amplifier section 23, and a power circuit 30.

Impedance converter 20 has a gate resistor R of 1 to 100 G ohms inserted into impedance converter FET (field effect transistor) Q1 to reduce output drift due to pyro-electricity. This results in a stable output during a change of temperature.

If constants of filter 21 are calculated in terms of a cut-off frequency of a high-pass filer determined by a minimum measuring frequency.

A last stage of filter 21 is connected to muting section MC 22 to make a rise of signal output quick just after power is turned on. Piezoelectric device 6 of circuit substrate 7 has circuit reference potential electrode 24 which can protect electricaly high impedance piezoelectric member 1 against electromagnetic noises.

Feed-through capacitors 25, 26, and 27 are inserted between the acceleration sensor of the present invention and external lines, such as power input and signal output to prevent external noises from entering the acceleration sensor.

Amplifier section 23 has temperature compensation circuit 28 to obtain stable sensitivity against a change of environmental temperature. It also has gain adjusting circuit 29 that can control the level of output signal Vo.

Power circuit 30 has a voltage withstanding device that can protect the acceleration sensor against possible reverse current. It also has an instantaneous voltage-down checking circuit and an instantaneous power-off checking circuit that can protect the acceleration sensor against possible voltage-down and power-off. Numbers 32 and 33 indicate a cable and a connector, respectively.

In the above-mentioned construction of the acceleration sensor according to the present invention, piezoelectric member 1 can be supported by circuit substrate 7 having a lower linear expansion coefficient than itself. This can keep constant the sensitivity of the acceleration sensor during a change of temperature.

Circuit substrate 7 can have component parts 19 mounted in signal processing electronic circuit 8 on the side thereof on which piezoelectric device 6 is not mounted.

Circuit substrates 7 and 7a are further fixed to cabinet 31. It is advantageous for securing it to use a soft adhesive agent, such as silicon resin or urethane resin. The adhesive agent can absorb possible strain due to a difference of linear expansion coefficients of both materials.

Figure 5:
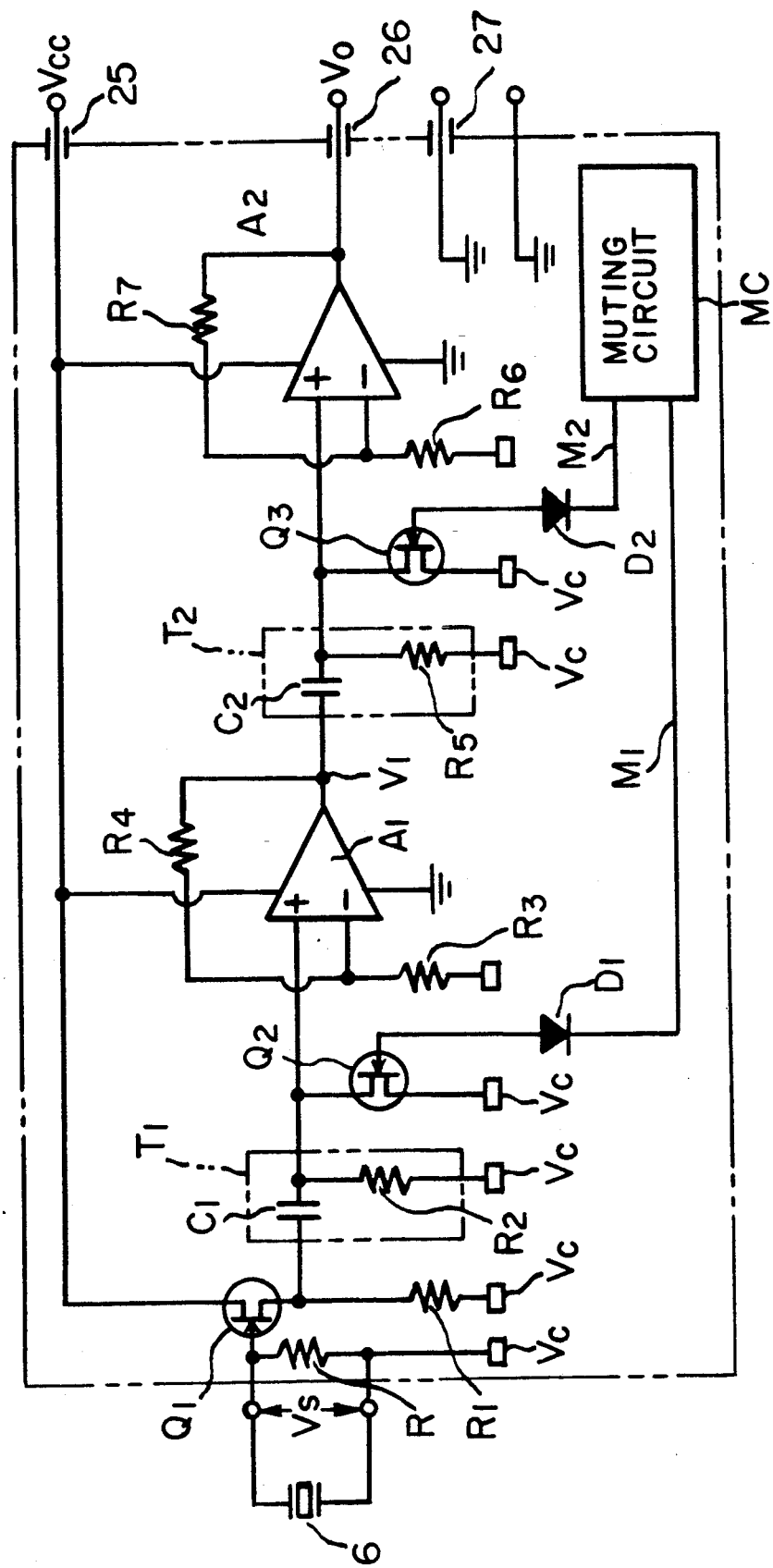
FIG. 5 is a schematic circuit diagram showing an example of a electronic circuit of the present invention.

FIG. 5 shows an example of the signal processing electronic circuit 8 according to the present invention. It comprises piezoelectric device 6, a circuit reference potential Vc, a voltage terminal Vcc, a gate resistor R, a source resistor R1, an impedance converter FET (field effect transistor) Q1, a first time constant circuit T1 consisting of a direct current blocking capacitor C1 and a resistor R2, a second time constant circuit T2 consisting of a direct current blocking capacitor C2 and a resistor R5. First time constant circuit T1 and second time constant circuit T2 form two filter devices, respectively. Signal processing electronic circuit 8 also comprises a first-stage amplifier A1, a second-stage amplifier A2, gain setting resistors R3 and R4 and gain setting resistors R6 and R7 that can set gains of the first-stage amplifier A1 and the second-stage amplifier A2, respectively and a temperature compensation circuit 28 (not shown). Signal processing electronic circuit 8 further comprises an impedance converter FET (field effect transistor) Q1 connected with resistor R2, switching device (field effect transistor) Q2 connected with resistor R5, a diode D1, a diode D2, and a muting section MC 22.

Figure 6:
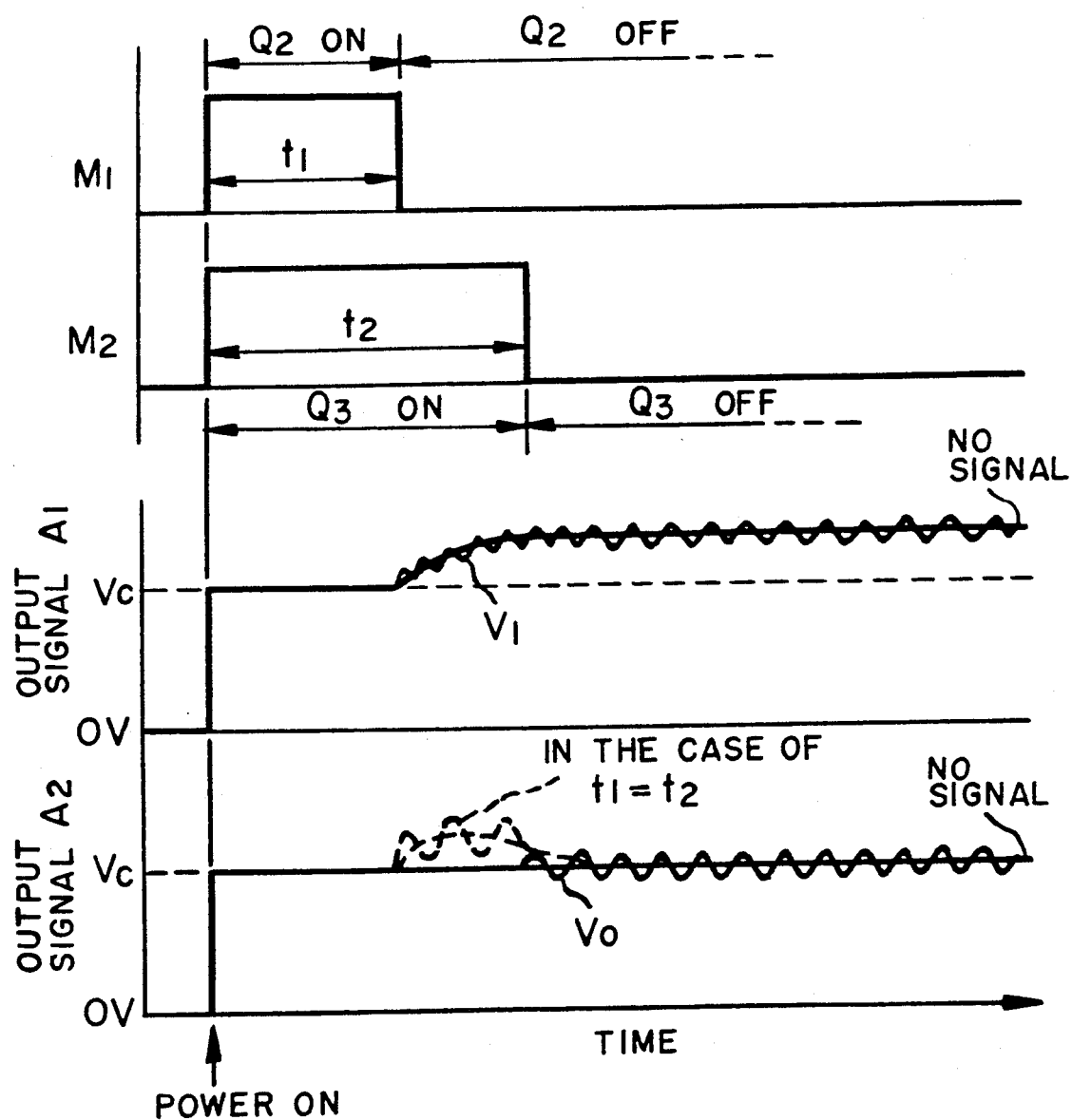
FIG. 6 is an illustrative graph of the operation of the electronic circuit.

Turn-on signal M1 of switching device (field effect transistor) Q2 and a muting turn-on signal M1 of switching device (field effect transistor) Q3 output of muting section MC 22, as shown in FIG. 6, are output at the same time as power is turned on. However, muting turn-on signal M1 can go off first; muting turn-off signal M2 can go off later.

Just after power is turned on, muting turn-on signal M1 and muting turn-off signal M2, pre-set higher than the circuit reference potential Vc, are applied to diodes D1 and D2, respectively. The FETs (field effect transistors) Q2 and Q3, then, can be turned on with voltages $V_{GS}$ between gates and source thereof set to 0 V by leakage currents of the diodes, respectively. When respective pre-set turn-on times t1 and t2 of the FETs (field effect transistors) Q2 and Q3 elapse, muting turn-on signal M1 and muting turn-off signal M2 become lower than respective pinch-off voltages of the FETs (field effect transistors) Q1 and Q2 as referenced to the circuit reference potential Vc. Then, FETs (field effect transistors) Q1 and Q2 turn off, respectively. It should be noted that turn-on time t1 is set shorter than t2.

In the circuit construction mentioned above, with power turned on, voltage terminal Vcc is applied to impedance converter FET (field effect transistor) Q1, first-stage amplifier A1, and second-stage amplifier A2. At the same time, muting section MC 22 is activated to output muting turn-om signal M1, which can turn on, for the period of time t1, switching device (field-effect transistor) Q2 connected in parallel with resistor R2 of first time constant circuit T1 through diode D1. When time t1 elapses, switching device (field-effect transistor) Q2 is turned off. Also, muting section MC22 is activated to output muting turn-on signal M1, which can turn on for a period of time t2 switching device (field-effect transistor) Q3 connected in parallel with resistor R5 of the first time constant circuit T2 through diode D2. When time t2 elapses, switching device (field-effect transistor) Q3 is turned off.

In the operation mentioned above, resistor R2 is apparently reduced to around 0 ohms for the period of time t1 by first time constant circuit T1. Thus, direct current blocking capacitor C1 can be quickly charged to a specific voltage. In t1, first time constant circuit T1 can transfer to first-stage amplifier A1 a sensor detected output signal Vs that was impedance-converted with a normal time constant thereof. Similarly, resistor R5 is apparently reduced to around 0 ohm for the period of time t2 by second time constant circuit T2. Thus, direct current blocking capacitor C2 can be quickly charged with a change of a direct current offset voltage of first-stage amplifier A1. In t2, the second time constant circuit T1 can transfer to the second-stage amplifier A2 a sensor detected output signal V1 that was amplified through the first-stage amplifier A1 with a normal time constant thereof.

As a result, a sensor amplifier output signal Vo is made to circuit reference potential Vc for the period of time t2 after power is turned on. It, then, becomes a stable amplified output signal of the sensor detected signal, which can make shorter a settling time lag to respond to the input signal. For example, if a low cut-off frequency is set at around 0.1 Hz, the sensor amplifier of the present invention requires around 6 seconds until the output is stable.

Piezoelectric device 6 and circuit substrates 7 and 7a are housed in the cabinet 31 comprising an internal conductive resin layer 10, an adiabatic resin layer 9, and an external conductive metal layer 11. Cable 32 is connected to feed-through capacitors 25, 26, and 27, and connector 33 is connected to cable 32.

The internal conductive resin layer 10 entirely encloses piezoelectric device 6 and signal processing electronic circuit 8 to protect them against possible electromagnetic noises. It is connected to a signal ground of signal processing electronic circuit 8. It is formed of a conductive resin of carbon and/or carbon fiber, a resin plating, a conductive paint, or similar matter. It also can contain a ferrite to shield those inner component parts against possible unnecessary radio-frequency signals.

Adiabatic resin layer 9 entirely encloses the inner component parts to prevent electricity focusing effect of piezoelectric member 1 from drifting the output signal to zero. It is formed of a resin, a foam resin, or similar materials having pleats.

External conductive matal layer 11 connected to the grounds of feed-through capacitors 25, 26, and 27 are connected to a metallic or similar matter to be measured to ground to protect the inner component parts against possible external radio-frequency noises.

The acceleration sensor of the present invention is described move specifically below. Piezoelectric member 1 uses a high polymer compound having the following composition.

Piezoelectric ceramic (PZT): 82.3 weight %.
Polyoxymethylene: 15.8 weight %.
NBR: 1.75 weight %.
Carbon: 0.13 weight %.

Piezoelectric member 1 is formed in a disk-like shape of 100 micrometers thick and 19 mm diameter.

Piezoelectric member 1 has positive electrode 2 of 13.5 mm diameter and negative electrode 3 of 14 mm inside diameter and 19 mm outside diameter on one side thereof and neutral electrode 4 on the other side of the entire area by printing with a conductive paint.

Neutral electrode 4 of piezoelectric member 1 has lining member 5 of glass epoxy resin of 19 mm diameter and 200 micrometer thick adhered with an epoxy adhesive agent so that the thickness of the adhesive agent layer can be thinner than 10 micrometer.

Piezoelectric device 6 is formed by supporting member 34 of a glass epoxy resin ring 1.2 mm thick, 19.5 mm outside diameter, and 15.5 mm inside diameter adhered to lining member 5 using an epoxy adhesive agent.

Piezoelectric device 6 is adhered to alumina circuit substrate 7 0.8 mm thick and 23 mm square having hybrid signal processing electronic circuit 8 using an epoxy adhesive agent.

Hybrid signal processing electronic circuit 8 has a connection circuit, a signal processing circuit, and a power circuit placed in position.

The above-mentioned circuit substrate 7 is contained in cabinet 31 formed of three layers, including internal conductive resin layer 10, insulative adiabatic resin layer 9, and external conductive metal layer 11, thereby completing the acceleration sensor of the present invention.

As understood from the above description, the acceleration sensor according to the present invention can reduce drift of the output thereof due to pyro-electricity and can make output Vo stable to a change of environmental temperature by the configuration of piezoelectric device 6 formed of piezoelectric member 1 having one or more electrodes provided on each side thereof and lining member 5 of low linear expansion coefficient adhered to one side thereof. Circuit substrate 7 of low linear expansion coefficient has the piezoelectric device 6 adhered to one side thereof and has signal processing electronic circuit 8 formed on the other side thereof, and cabinet 31 having three layers, including internal conductive resin layer 10, adiabatic resin layer 9, and external conductive metal layer 11, which entirely enclose piezoelectric device 6 and circuit substrate 7.

Also, the acceleration sensor can make the sensitivity thereof constant irrespective of a change of environmental temperature by a configuration of circuit substrate 7 with a linear expansion coefficient less than that of piezoelectric member 1 supporting the piezoelectric device 6.

Further, the acceleration sensor can absorb any possible strain due to differences of the linear expansion coefficients of circuit substrate 7 and the three layers, including internal conductive resin layer 10, adiabatic resin layer 9, and external conductive metal layer 11, by a configuration of soft adhesive agent used to secure circuit substrate 7 to three layers.

Furthermore, the acceleration sensor cannot only protect the signal processing electronic circuit 8 against possible electromagnetic noises by a configuration of piezoelectric device 6 and circuit substrate 7 entirely enclosed by internal conductive resin layer 10 connected to the signal ground of signal processing electronic circuit 8, but also can eliminate the effect due to the radio-frequency electromagnetic waves by a configuration of external conductive matal layer 11 connected to grounding terminals of the feed-through capacitors 25, 26, and 27.

Moreover, the acceleration sensor can be constructed to be simple, compact and small in size by a configuration of signal processing electronic circuit 8 having the capacitor for preventing possible external inductive noises incorporated therein.

Particularly, piezoelectric device 6 provides a constant sensitivity gradient with temperature since lining member 5 and supporting member 34 provide a great contribution in connection with vibration.

It will be understood that the present invention is not limited to the specific embodiments herein before discussed but extends to all modifications thereof which will occur to those skilled in the art upon consideration of the general disclosure, its illustrative details and the scope of the claims appended hereto.

The above description of the preferred embodiment of this invention and the preferred dimensions thereof are given by way of example only, and numerous modifications can be made by those familiar with acceleration sensors without departing from the scope of the invention as defined in the claims. Indeed, the suggested dimensions are preferred only for the acceleration sensor indicated, and these dimensions should be modified accordingly to accommodate the piezoelectric device of different dimensions or configurations.

The embodiments of the invention in which an exclusive property or privilege is claimed are defined as follows:

1. An acceleration sensor including, a piezoelectric device (6) which is formed of a piezoelectric member (1) having one or more electrodes provided on each of side thereof and a lining member (5) having a low linear expansion coefficient adhered to one side thereof, a circuit substrate (7) of low linear expansion coefficient having the piezoelectric device (6) adhered to one side thereof and having a signal processing electronic circuit (8) formed on the other side thereof, and a cabinet (31) having three layers, including an internal conductive resin layer (10), an adiabatic resin layer (9), and an external conductive metal layer (11), which entirely encloses the piezoelectric device (6) and the circuit substrate (7).

2. An acceleration sensor according to claim 1, in which the lining member (5) has a supporting member (34) of linear expansion coefficient equal to or less than that thereof adhered to a circumference thereof.

3. An acceleration sensor of the character claimed in claim 1, in which the piezoelectric member (1) of the piezoelectric device (6) has a pair of electrodes, including a positive electrode (2) and a negative electrode (3), provided on one side thereof, and a neutral electrode (4) provided on the other side thereof, the neutral electrode (4) having the lining member (5) adhered thereto, the lining member (5) having the supporting member (34) adhered to a circumference thereof.

4. An acceleration sensor according to claim 1, in which an output of the piezoelectric device (6) is connected to an impedance converter (20), a by-pass filter (21), and an amplifier section (23) of the signal processing electronic circuit (8), the by-pass filter (21) and the amplifier section (23) having a muting section (MC 22), a power circuit (30) provided to supply power to the circuits mentioned above, and an output of the amplifier section (23), an input of the power circuit (30), and a signal ground of the signal processing electronic circuit (8) having feed-through capacitors (26), (25), and (27) inserted respectively.

5. An acceleration sensor according to claim 1, in which the piezoelectric member (1) is formed of a high polymer piezoelectric material.

6. An acceleration sensor according to claim 1, in which the piezoelectric member (1) has a positive electrode (2) provided on one side thereof and a negative electrode (3) provided on the other side thereof.

7. An acceleration sensor according to claim 1, in which the piezoelectric member (1) has the positive electrode (2) provided on a central portion of one side thereof and the negative electrode (3) provided on a circumferential portion of the other side thereof.

8. An acceleration sensor according to claim 2, in which the lining member (5), the supporting member (34), and circuit substrate (7) have respective communication holes so that a space enclosed by them can communicate with an outside environment.

9. An acceleration sensor according to claim 8, in which the circuit substrate (7) has feed-through holes (17) and (18).

10. An acceleration sensor comprising:
a piezoelectric device (6) comprised of a piezoelectric member (1) having one or more electrodes formed on either side thereof, lining means (5) having a low linear coefficient of expansion bonded to one side of said piezoelectric member (1);
circuit substrate means (7) having a low linear expansion coefficient;
bonding means adhering said piezoelectric oscillator device (6) to said circuit substrate means (7),
enclosure means having an internal conductive resin layer (10), an adiabatic resin layer (9), and an outer metallic layer entirely enclosing said piezoelectric oscillator device (6) and circuit substrate means (7),
whereby a stable oscillation sensor is formed.

11. The sensor according to claim 10 in which said lining means (5) includes circumferential support means, said circumferential support means (34) having a linear coefficient of expansion equal to or less than the lining means (5).

12. The sensor according to claim 10 in which said piezoelectric member (1) has a pair of electrodes (2, 3) provided on one side thereof, one of said electrodes being a positive electrode (2) and the other being a negative electrode (3) and a neutral electrode (4) on the other side opposite said pair of electrodes (2, 3), said lining means (5) with said circumferential support (34) being adhered to the other with said neutral electrode (4).

13. The sensor according to claim 10 in which an output terminal of said piezoelectric oscillator is connected to a signal processing circuit (8) composed an impedance converter (20), a by-pass filter (21) and an amplifier (23), said amplifier (23) having muting means (22), power supply means (30) providing power to said signal processing circuit, and three feed through capacitors (25, 26, 27), connected to the circuit of said amplifier (23), the input of power supply means (30) and signal ground of signal processing circuit (8).

14. The sensor according to claim 10 in which said piezo electric member is comprised of a high polymer piezoelectric material.

15. The sensor according to claim 10 in which said electrodes comprise a positive electrode (2) on one side of said piezoelectric member and a negative electrode on the other.

16. The sensor according to claim 10 in which said electrodes comprise a centrally located positive electrode (2) on one side of said piezoelectric member and a circumferential negative electrode (3) around said centrally located electrode (2).

17. The sensor according to claim 11 in which said lining means (5), said supporting means (34) and said circuit substrate (7) have respective communication holes to allow the space between them to communicate with an outside environment.

18. The sensor according to claim 17, in which said circuit substrate (7) has feed through holes (17, 18).

* * * * *